United States Patent
Franklin et al.

(10) Patent No.: US 6,231,841 B1
(45) Date of Patent: May 15, 2001

(54) ANTIPERSPIRANT COMPOSITIONS

(75) Inventors: Kevin Ronald Franklin; Lynda Grainger; Adam Jan Kowalski, all of Bebington (GB)

(73) Assignee: Unilever Home & Personal Care USA, division of Conopco, Inc., Chicago, IL (US)

( * ) Notice: Subject to any disclaimer, the term of this patent is extended or adjusted under 35 U.S.C. 154(b) by 0 days.

(21) Appl. No.: 09/547,625

(22) Filed: Apr. 12, 2000

(30) Foreign Application Priority Data

Apr. 12, 1999 (GB) .................................. 9908208

(51) Int. Cl.⁷ .............................. A61K 7/32; A61K 7/34; A61K 7/38; A61K 7/00
(52) U.S. Cl. ................................ 424/65; 424/66; 424/68; 424/400; 424/401
(58) Field of Search .................. 424/65, 66, 68, 424/400, 401

(56) References Cited

U.S. PATENT DOCUMENTS 5,403,580   4/1995   Bujanowski et al. .

FOREIGN PATENT DOCUMENTS

97/11678   4/1997   (WO) .
97/42830   11/1997  (WO) .
98/34588   8/1998   (WO) .

OTHER PUBLICATIONS

European Search Report Application No. EP 99 30 4462 dated Jul. 18, 2000.
Chemical Abstract vol. 115, No. 22, "Cosmetics Containing Thermosensitive Cholesteric Liquid Crystals"—Abstract No. 239306—XP 002141805 & JP 03 034907—Pola Chemical Industries, Inc. Dec. 2, 1991.

Primary Examiner—Shelley A. Dodson
(74) Attorney, Agent, or Firm—Matthew Boxer

(57) ABSTRACT

Antiperspirant compositions herein comprise an antiperspirant active, a carrier and a structurant for the carrier which comprises an effective concentration of a combination of at least one sterol and at least one sterol ester, to form a solid or a soft solid. The compositions can be anhydrous and in the form of a suspension of antiperspirant active, or can comprise aqueous emulsions.

A particularly suitable sterol comprises β sitosterol and a particularly preferred sterol ester comprises oryzanol. Preferably the mole ratio of sterol to sterol ester is in the range of 3:1 to 1:2.

30 Claims, No Drawings

ANTIPERSPIRANT COMPOSITIONS

RELATED APPLICATIONS

The following U.S. patent applications are co-pending with, and commonly assigned with, the present application:

U.S. Ser. No. 09/548,309 to Franklin et al., filed Apr. 12, 2000;

U.S. Ser. No. 09/548,310 to Franklin et al., filed Apr. 12, 2000;

U.S. Ser. No. 09/547,804 to Franklin et al., filed Apr. 11, 2000;

U.S. Ser. No. 09/547,604 to Franklin et al., filed Apr. 12, 2000;

U.S. Ser. No. 09/547,445 to Esser et al., filed Apr. 12, 2000; and

U.S. Ser. No. 09/592,130 to Franklin et al., filed Jun. 12, 2000.

TECHNICAL FIELD

The present invention relates to antiperspirant compositions and in particular to thickened or structured compositions.

BACKGROUND AND PRIOR ART

Topically applied antiperspirant compositions are in widespread use throughout much of the world, in order to enable their users to avoid or minimise visible wet patches on their skin, especially in axillary regions. Antiperspirant formulations have been applied using a range of different applicators, including aerosols, roll-ons, pump sprays, sticks and mushroom applicators, in accordance with the individual preferences of consumers. In some parts of the world, sticks are especially popular. The term stick traditionally indicates a bar of solid material which was usually housed within a dispensing container and which retains its integrity whilst being applied, a firm stick. When a portion of a firm stick is drawn across the skin surface, a film of the stick composition is transferred onto the skin surface. Although the stick has the appearance of a solid article, the material forming the stick usually comprises a structured liquid phase such that a film of the material is readily transferred onto another surface upon contact under pressure.

More recently, the term has been applied to soft solids, which have an apparent solid form during storage, but which flow under mild pressure or shear, so that in use they can be extruded through an aperture or apertures onto a dispensing surface. Soft solids retain their shape for at least 30 seconds if removed under non-shear/stress conditions from a container, but if subjected to shear or stress, their structure is destroyed and no more than a minor fraction of the structure can be reformed within a period of about 24 hours when the shear/stress is removed.

There are typically three classes of antiperspirant sticks, namely suspension sticks, emulsion sticks and solution sticks. Suspension sticks contain a particulate antiperspirant active material suspended in a structured carrier. Emulsion sticks normally comprise an emulsion of an oil phase and a hydrophilic phase containing the antiperspirant active in solution, the continuous phase being structured. In some emulsion sticks, the continuous phase is an oil phase. In solution sticks, the antiperspirant is typically dissolved in the liquid carrier phase which is structured. The liquid phase can comprise water and/or a water-miscible organic solvent. The three categories can be applied to sticks of both firm and soft solids compositions.

Conventionally, many sticks have been structured using naturally-occurring or synthetic waxes, of which typical examples include stearyl alcohol, and hydrocarbon waxes or silicone waxes. Waxes are widely available, and by suitable selection of the waxes themselves and their concentrations in the formulation can effectively obtain either a soft solid or a firm solid. Thus for example, wax-structured sticks are described in an article in Cosmetics and Toiletries, 1990, vol 105, p75–78. However, fatty alcohol or wax structured sticks tend to leave visible white deposits on application to human skin, and the deposits can also be transferred onto clothing by physical contact with the skin. A significant, and possibly growing, proportion of consumers of antiperspirants have indicated displeasure at visible deposits. Accordingly, the antiperspirant industry, including the instant inventors, is devoting considerable time and resources to finding means to ameliorate or overcome the customer perception of whiteness deposits.

A number of alternative structurants to waxes have been proposed. The term "gellant" is often employed instead of "structurant". Where the resultant product is a liquid of increased viscosity rather than a solid or gel, the term "thickener" can also be used. For example, the use of dibenzylidene sorbitol (DBS) or derivatives thereof has been proposed as gellant in a number of publications, such as EP 0512770, WO 92/19222, U.S. Pat. Nos. 4,822,602 and 4,725,430. Formulations containing such gellants can suffer from a number of disadvantages, including instability in the presence of acidic antiperspirants, and comparatively high processing temperatures needed in the production of sticks. Some of such formulations containing such gellants are sticky or tacky.

A combination of an n-acylaminoacid amide and 12-hydroxystearic acid to gel a non-aqueous formulation is described in WO 93/23008 and U.S. Pat. No. 3,989,087. However, high processing temperatures are needed to dissolve the gellants and prevent premature gelling. When applied to the skin the formulation can be difficult to wash off, reformulation to overcome the latter problem can be made impossible by the need for high processing temperature.

In WO 97/11678 to Helene Curtis, Inc, there is described the use of a sterol and particularly lanosterol as gellant, sometimes in conjunction with a starch hydrolyzate derivative for antiperspirant compositions.

In WO 98/34588 to Lancaster Group GmbH, there is described the use of lanesterol as a gellant for oil-based cosmetic compositions, containing a cosmetic active material, of which one listed material is a deodorant, though not exemplified.

OBJECTS OF THE INVENTION

It is an object of the present invention to ameliorate or overcome one or more of the foregoing disadvantages of structured sticks. A particular object of the invention, in at least one aspect, comprises providing a stick exhibiting low visible deposits gelled by a non-wax system.

SUMMARY OF THE INVENTION

According to the present invention there is provided an antiperspirant composition comprising an antiperspirant active, a liquid carrier and a structurant including a sterol to thicken or solidify the composition characterised in that the structurant comprises an effective concentration of a combination of at least one sterol and at least one sterol ester.

The combination of the sterol and the sterol ester in a suitable mole ratio enables the hydrophobic liquid carrier in the antiperspirant formulation to be structured effectively and in a readily controllable manner. The invention combination of gellants, a twin gellant system, has demonstrated superior gelation in comparison with either constituent. Without being bound to any specific theory or explanation as to why the combination is so effective, it is believed that the sterol and sterol ester constituents stack with each other to form a network of strands, the stacking possibly being regular. The presence of both constituents in the stacking appears to encourage the growth of the strands and result in a network which is superior to that from either constituent alone.

The employment of the twin gellant system can avoid or at least ameliorate a potential problem of premature gelation which can sometimes arise if a single gellant system is employed, for example by controlling the manner and timing in which the two components of the twin gellant system are mixed with the phase to be gelled.

DETAILED DESCRIPTION OF THE INVENTION

The invention formulation comprises as essential constituents
a) a sterol/sterol ester gellant system in addition to;
b) an antiperspirant active and
c) a liquid carrier The sterol/sterol ester gellant system comprises the sterol and sterol ester in a mole ratio that is normally selected in the range of from 10:1 to 1:10, especially from 6:1 to 1:4 and preferably in the range of from 3:1 to 1:2. Employment of the two system constituents within such a mole ratio range, and especially within the preferred range facilitates the co-stacking of the constituents and consequently facilitates the formation of a network that is readily able to structure the formulation.

The invention twin gellant system is desirably present at a concentration of greater than 0.5%, and preferably greater than 1%. It is normally present at a concentration of up to 20%, and in many preferred embodiments of not more than 15%. Concentrations herein are expressed by weight based on the formulations, unless explicitly otherwise stated, be they for the gellant system or some other constituent. Except in operative or comparative examples, all numbers herein indicating amounts or ratios of materials, such as limits of ranges are to be understood as modified by about, unless expressly stated otherwise.

The hardness of the stick or viscosity of the formulation varies depending, amongst other parameters, on both the concentration of the twin gellant system and the choice of mole ratio of the two constituents of the system. For preparing a soft solid, it is preferable to employ the system at a concentration in the range of from 1.2 to 2.75% and a higher concentration to prepare a solid, particularly from 3.5 to 9%. The formulation tends to demonstrate greater hardness as the ratio of sterol to sterol ester increases. This property is of notable benefit, since it enables the hardness of the product formulation can be fined tuned whilst allowing the overall concentrations of the gellant system and the remaining constituents of the formulation to remain unchanged.

Herein, the sterol comprises a polycyclic alcohol containing at least 24 carbon atoms and contains at least 4 condensed rings, each ring having at least 3 carbon atoms and preferably from 3 to 6 carbon atoms, and especially 5 or 6 carbon atoms. The ring system can be saturated or may contain at least one degree of unsaturation. In a number of desirable sterols, the rings are approximately planar and in yet other desirable sterols the hydroxyl substituent is equitorial. Preferably, the sterol does not comprise lanesterol.

In particularly preferred embodiments, the sterol satisfies either of the formulae:

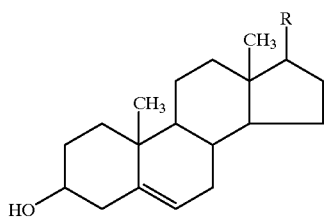

(1)

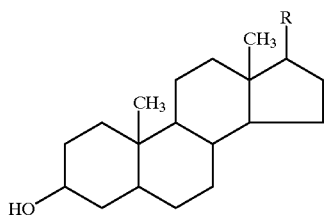

(2)

in which R represents an aliphatic, cycloaliphatic or aromatic group, and preferably a linear or branched aliphatic saturated or unsaturated hydrocarbon group. R desirably contains from 1 to 20 carbons and preferably from 4 to 14 carbons.

It is particularly suitable to employ β sitosterol or campesterol or cholesterol, or a hydrogenated derivative thereof, such as dihydrocholesterol, or a mixture of two or more of them. An especially preferred sterol is β sitosterol.

The sterol ester employed herein is advantageously an ester of the sterols described hereinabove with a phenolic acid. The term phenolic acid as employed herein relates to the family of cinnamic acid, such as caffeic acid and ferulic acid. Beneficial results have been obtained when the ring structure of the sterol ester matches the ring structure of the sterol, for example in terms of the number, size and relative positioning of the fused rings. The sterol ester preferably is substituted by an aliphatic, cycloaliphatic or aromatic group at a ring carbon remote from the ester substituent, and most preferably the relative spacing of the ester group from that aliphatic, cycloaliphatic or aromatic group in the sterol ester is the same as the spacing of the hydroxyl group from that aliphatic, cycloaliphatic or aromatic group in the sterol. It is highly desirable to employ a hydrocarbon substituent which may be linear or branched and saturated or unsaturated, containing from 2 to 20 and particularly 4 to 14 carbons. A convenient subclass of substituent comprises branched hydrocarbons containing from 5 to 10 carbon atoms and one degree of unsaturation.

It is particularly suitable to employ as the sterol ester, oryzanol, sometimes referred to as γ oryzanol which consists of a mixture of ferulic acid esters of unsaturated triterpene alcohols, and contains material satisfying the following formula (3):

be zero. Some especially preferred halohydrate salts comprise activated aluminium chlorohydrates such as those described in EP-A-6739 (Unilever NV et al), the contents of which specification is incorporated herein by reference.

Activated salts retain their enhanced activity and are advantageously employed in substantially anhydrous formulations, i.e. formulations which do not contain a distinct aqueous phase. Some activated salts can also retain their enhanced activity in hydrous formulations too.

A range of zirconium salts which can be employed desirably in antiperspirant compositions herein is represented by the following empirical general formula: $ZrO(OH)_{2n-nz}B_z.wH_2O$ in which z is an integer or non-integer in the range of from 0.9 to 2.0, n is the valency of B,

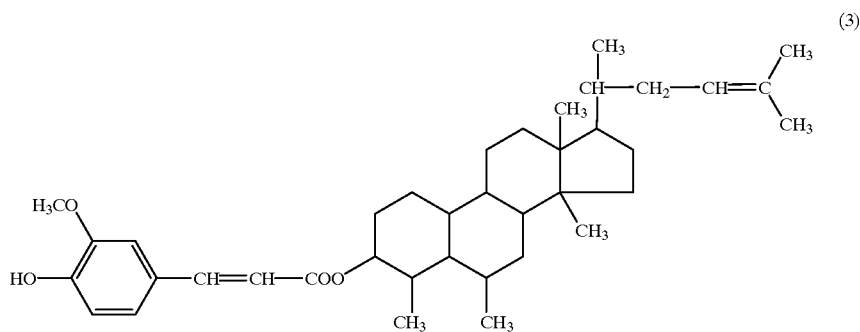

(3)

An especially preferred twin gellant system comprises β sitosterol and γ oryzanol, advantageously within the ranges of mole ratios described hereinbefore.

The invention combination of sterol plus sterol ester forms a network of interconnected strands or fibres extending throughout the hydrophobic carrier liquid or hydrophobic phase if the carrier liquid further comprises a dispersed polar phase. The interconnecting fibres are generally thin, a diameter typically less than 0.5 μm and often less than 0.2 μm and has numerous branches or interconnections.

For use in an unrelated field, there is described in WO 97/42830 to Unilever NV the addition of two different specific sterols, preferably phytosterols to increase the firmness of liquid fats, such as edible fats, without any suggestion that such sterols be contemplated to gel a liquid carrier in antiperspirant compositions.

The second essential constituent of the invention compositions is an antiperspirant active. Antiperspirant actives, are preferably. incorporated in an amount of from 0.5–60%, particularly from 5 to 30 or 40% and especially from 10 to 30 or 35%.

Antiperspirant actives for use herein are often selected from astringent active salts, including in particular aluminium salts, zirconium salts and mixed aluminium-zirconium salts, including for each both inorganic salts and organic salts and complexes. Preferred astringent salts include aluminium, zirconium and aluminium-zirconium halides and halohydrate salts, such as chlorohydrates.

Preferred aluminium salts include aluminium halohydrates having the general formula $Al_2(OH)_xQ_y.wH_2O$ in which Q represents chlorine, bromine or iodine, x is from 2 to 5 and x+y=6, x and y being either integers or non-integers and w represents a variable amount of hydration, which may 2–nZ is at least 0, B is selected from the group consisting of halides, including chloride, sulphamate, sulphate and mixtures thereof and w represents a variable amount of hydration, which may be zero. In preferred zirconium salts B represents chloride and z lies in the range of from 1.5 to 1.87. In practice, such zirconium salts are usually not employed by themselves, but as a component of a combined aluminium and zirconium-based antiperspirant, the aluminium component normally being selected in accordance with the above-mentioned formula for halohydrates. Especially desirable salts comprise mixed aluminium-zirconium chlorohydrates, optionally activated.

It will be recognised that the above-identified formulae for aluminium, zirconium and aluminium-zirconium salts are empirical and encompass compounds having coordinated and/or bound water in various quantities as well as polymeric species and mixtures and complexes. In particular, zirconium hydroxy salts often represent a range of salts having various amounts of the hydroxy group.

Antiperspirant complexes based on the above-mentioned astringent aluminium, zirconium and aluminium-zirconium salts can desirably be employed in the present invention. Preferably, aluminium halohydrate and/or zirconium chlorohydrate materials are complexed. The complex often employs a carboxylic acid or carboxylate group, and advantageously an aminoacid. Examples of suitable aminoacids include dl-tryptophane, dl-β-phenylaniline, dl-valine, dl-methionine and β-aniline, and preferably glycine which satisfies the formula $CH_3CH(NH_2)CO_2H$.

It is highly desirable to employ complexes of a combination of aluminium halohydrates and zirconium chlorohydrates together with aminoacids such as glycine, such as those disclosed in U.S. Pat. No. 3,792,068 (Luedders et al).

Certain of those Al/Zr complexes are commonly called ZAG in the literature. ZAG actives generally contain aluminium, zirconium and chloride with an Al/Zr ratio in the range of 2 to 10, especially 2 to 6, a ratio of (Al—Zr)/Cl in the range of 2.1 to 0.9 and a variable amount of an amino acid, particularly glycine. Actives of this preferred type are available from Westwood, Summit and Reheis.

In some formulations, it is particularly preferably to employ activated ZAG complexes which can be produced by the process disclosed in U.S. Pat. No. 5,486,347 (Callaghan et al).

Other actives which can be utilised comprise aluminium lactates, borate cross-linked aluminium salts, and astringent titanium salts, for example those described in GB 2299506A. Yet other actives includes chlorlinergenics, antihistamines and antiandrenerics.

The proportion of solid antiperspirant salt in the composition normally includes the weight of any water of hydration and any complexing agent that may also be present. However, when the antiperspirant salt is dissolved in aqueous solution, it's weight excludes any water present.

In some embodiments of the present invention, the antiperspirant salts is employed herein in particulate form, and particularly in compositions which do not comprise an aqueous or hydrophilic phase. Such compositions are conveniently referred to as anhydrous or substantially anhydrous. The particle size of antiperspirant salts in such compositions often falls within the range of 1 to 200 μm with a mean particle sizes often from 3 to 20 μm, such as when conventional barrels are filled using conventional cast processes. Both larger and smaller mean particle sizes can also be contemplated such as from 20 to 50 μm or 0.1 to 3 μm.

In other embodiments, the antiperspirant active can be employed in solution form, for example where the composition comprises a polar phase, normally comprising water and/or a water-miscible solvent. In such embodiments, the concentration of antiperspirant active in solution (in the disperse polar phase) is often in the range of from 3 to 60%, based on solely the polar phase, particularly from 10% or 20% up to 55% or 60% of that phase.

The third essential constituent of the composition is a liquid carrier, often in a proportion of from 20 to 95% of the composition, and particularly from 40 to 90%.

The carrier that is incorporated in compositions herein comprises one or more materials that is liquid at which the composition is used and can be gelled or otherwise structured by the structurant to provide a firm or extrudable solid at that use temperature, which conventionally is residential ambient, which is usually below 40° C. and in many instances below 30° C. and often at least 15° C. The carrier can be hydrophobic or a mixture of both hydrophobic and hydrophilic, the latter normally being in the form of an emulsion. It is particularly desirable that the carrier herein contains sufficient hydrophobic material to produce a continuous phase in which a discontinuous hydrophilic phase or particulate phase can be dispersed. The twin gellant system of the present invention is suited especially to gelling a hydrophobic medium and can also structure a dispersed oil phase, should that be present.

The hydrophobic carrier liquid may have some volatility or contain volatile constituents but generally its vapour pressure will be less than 4 kPa at 25° C., so that it can be described as an oil or mixture of oils. More specifically, it is desirable that at least 80% by weight of the hydrophobic carrier liquid should consist of materials having a vapour pressure not above 4 kPa at 25° C.

One class of carriers that is particularly desirable herein is hydrophobic and comprises liquid silicones, in order to promote good sensory properties at the time of use of the formulation. Preferably at least a major fraction of the silicone carrier is constituted by at least one volatile polyorganosiloxane, i.e. liquid materials having a measurable vapour pressure at ambient conditions (about 20 to 25° C.). Typically the vapour pressure of volatile silicones lies in the range of from 1 or 10 Pa to 2 kPa at 25° C. Volatile polyorganosiloxanes can be linear or cyclic or mixtures thereof. Preferred cyclic siloxanes include polydimethylsiloxanes and particularly those containing from 3 to 9 silicon atoms and preferably not more than 7 silicon atoms and most preferably from 4 to 6 silicon atoms, otherwise often referred to as cyclomethicones. Preferred linear siloxanes include polydimethylsiloxanes containing from 3 to 9 silicon atoms. The volatile siloxanes normally by themselves exhibit viscosities of below $1 \times 10^{-5}$ m$^2$/sec (10 centistokes), and particularly above $1 \times 10^{-7}$ m$^2$/sec (0.1 centistokes), the linear siloxanes normally exhibiting a viscosity of below $5 \times 10^{-6}$ m$^2$/sec (5 centistokes). The volatile silicones can also comprise branched linear or cyclic siloxanes such as the aforementioned linear or cyclic siloxanes substituted by one or more pendant —O—Si(CH$_3$)$_3$ groups. Examples of commercially available silicone oils include oils having grade designations 344, 345 244, 245 and 246, (from Dow Corning Corporation).

Silicone 7207 and Silicone 7158 (from Union Carbide Corporation) and SF1202 (from General Electric [US]). Volatile silicones are often present in the composition in a proportion of up to 80% particularly from 10 to 70% and in a number of instances from 20 to 60%.

The hydrophobic carrier employed in compositions herein can alternatively or additionally comprise non-volatile silicone oils, which include polyalkyl siloxanes, polyalkylaryl siloxanes and polyethersiloxane copolymers. These can suitably be selected from dimethicone and dimethicone copolyols. Commercially available non-volatile silicone oils include Dow Corning 556 and Dow Corning 200 series. Non-volatile silicones are often present in not more than about 30% by weight of the composition, and preferably from 1 to 15% by weight. In many instances, when a non-volatile silicone oil is present, its weight ratio to volatile silicone oil is chosen in the range of from 1:3 to 1:40.

Silicon-free hydrophobic organic carriers can be incorporated in the invention compositions in addition to or instead of liquid silicones, i.e. from 0 to 100% of the hydrophobic carrier liquids. Such silicon-free hydrophobic organic carrier materials can include liquid aliphatic hydrocarbons such as mineral oils or hydrogenated polyisobutene, often selected to exhibit a low viscosity. Further examples of liquid hydrocarbons comprise polydecene and isoparaffins containing at least 10 carbon atoms.

Other suitable hydrophobic carriers comprise liquid aliphatic or aromatic esters, as a fraction of the water-immiscible carrier, desirably not more than 20% and in many instances less than 10% of the weight of the water-immiscible carrier.

Suitable aliphatic esters contains at least one long chain alkyl group, such as esters derivable from $C_1$–$C_{20}$ alkanols esterified with a $C_8$ to $C_{22}$ alkanoic acid or $C_6$ to $C_{10}$ alkanedioic acid. The alkanol and acid moieties or mixtures thereof are preferably selected such that they have a melting point of below 20° C. Suitable esters include isopropyl myristate, lauryl myristate, isopropyl palmitate, diisopropyl sebacate and diisopropyl adipate.

Suitable liquid aromatic esters, preferably having a melting point of below 20° C., including fatty alkyl benzoates. Examples of such esters include suitable C8 to C18 alkyl benzoates or mixtures thereof.

Further instances of suitable hydrophobic carriers comprise liquid aliphatic ethers derivable from at least one fatty alcohol, such as myristyl ether derivatives e.g. PPG-3 myristyl ether or lower alkyl ethers of polyglycols such as PPG-14 butyl ether. The proportion of ether in a formulation according to the present invention is often selected in the range of from 0 to 40% w/w and in some formulations particularly from 1 to 30% w/w.

Yet other suitable hydrophobic carriers comprise liquid aliphatic alcohols containing at least 10 carbon atoms which are liquid at 20° C. Examples of such alcohols include branched chain alcohols such as ethylhexyl alcohol, octyldodecanol and isostearyl alcohol. The proportion of the alcohol in a formulation according to the present invention is often selected in the range of from 0 to 40% w/w and particularly from 1 to 30% w/w. Aliphatic alcohols which are solid at 20° C. are preferably absent or present at a low concentration such as less than 5% w/w of the whole composition, since such alcohols can lead to visible white deposits from topical employment of the composition.

The total proportion of non-silicone hydrophobic carrier(s) is often chosen in the range of from 0 to 80% and particularly from 5 to 70% by weight. Mixtures of hydrophobic non-silicone organic carriers can be employed. If oxygen-containing silicon-free hydrophobic organic liquids are employed, they desirably constitute not more than 70% by weight of the hydrophobic carrier. Lower proportions of the hydrophobic phase, ranging up to for example 20, 30 or 35% in total by weight are more likely.

Mixtures of silicone and non-silicone carriers can suitably be employed herein, in any weight ratio, and in a number of tested embodiments the ratio lies in the range of from 20:1 to 1:20.

The carrier or mixture of carrier employed in the present invention can be and in many effective compositions is anhydrous, i.e. contain no free water, by employing solely one or more hydrophobic carriers. Alternatively, if desired, the composition can comprise a hydrophilic carrier, such as in particular water and/or a water-miscible organic solvent such as an alcoholic water-miscible solvent, in addition to a hydrophobic carrier, such as those indicated hereinbefore. Compositions containing both a hydrophobic and a hydrophylic carrier normally have one of them as a disperse phase. Formulations containing a disperse phase in practice would often further comprise an emulsifying surfactant, such as an anionic, cationic, zwitterionic and/or nonionic surfactant.

In emulsions herein, the polar disperse phase, including any material dissolved therein, normally constitutes from 5 to 80% of the weight of the composition and in many embodiments up to 50 or 60% by weight and such or other embodiments preferably at least 25% by weight by weight. The continuous phase containing structurant therefore provides the weight balance of the composition, such as from 20 to 95% by weight. The emulsions herein normally comprises a water in oil emulsion, i.e. the disperse phase is the hydophilic phase. Where an emulsion is employed, it can be convenient to prepare an emulsion in a separate step before it is mixed with the remaining constituents of the composition to produce the complete formulation.

The emulsion in many instances incorporates one or more emulsifiers, which often are non-ionic. The proportion of emulsifier or emulsifier system, i.e. combination of emulsifiers, in the emulsion is often selected in the range of from 0.1 to 10% w/w, and in many instances from 0.25 to 5% w/w. Most preferred is an amount of from 0.1 or 0.25% up to 3% w/w. It is desirable to employ an emulsifier or emulsifier system providing an overall HLB value in a range of from 2 to 10 and preferably from 3 to 8.

It may be convenient to employ an emulsifier system employing in combination an emulsifier having an HLB value above a desired overall value and one having an HLB value below the desired value. By employing the two emulsifiers together in appropriate ratios, it is readily feasible to attain a weighted average HLB value that promotes the formation of an emulsion.

Many suitable emulsifiers are nonionic ester or ether emulsifiers comprising a polyoxyalkylene moiety, especially a polyoxyethylene moiety, often containing from about 2 to 80, and especially 5 to 60 oxyethylene units, and/or contain a polyhydroxy compound such as glycerol or sorbitol or other alditols as hydrophilic moiety. The hydrophilic moiety can contain polyoxypropylene. The emulsifiers additionally contain a hydrophobic alkyl, alkenyl or aralkyl moiety, normally containing from about 8 to 50 carbons and particularly from 10 to 30 carbons.

The hydrophobic moiety can be either linear or branched and is often saturated, though it can be unsaturated, and is optionally fluorinated. The hydrophobic moiety can comprise a mixture of chain lengths, for example those deriving from tallow, lard, palm oil sunflower seed oil or soya bean oil. Such non-ionic surfactants can also be derived from a polyhydroxy compound such as glycerol or sorbitol or other alditols. Examples of emulsifiers include ceteareth-10 to -25, ceteth-10–25, steareth-10–25, and PEG-15–25 stearate or distearate. Other suitable examples include C10–C20 fatty acid mono, di or tri-glycerides. Further examples include C18–C22 fatty alcohol ethers of polyethylene oxides (8 to 12 EO).

The co-emulsifiers, which typically have a low HLB value, and often of from 2 to often comprise mono or possibly fatty acid diesters of polyhydric alcohols such as glycerol, sorbitol, erythritol or trimethylolpropane. The fatty moiety is often from C14 to C22 and is saturated in many instances, including cetyl, stearyl arachidyl and behenyl. Examples include monoglycerides of palmitic or stearic acid, sorbitol mono or diesters of myristic palmitic or stearic acid, and trimethylolpropane monoesters of stearic acid.

A particularly desirable class of emulsifiers comprises dimethicone copolymers, namely polyoxyalkylene modified dimethylpolysiloxanes. The polyoxyalkylene group is often a polyoxyethylene (POE) or polyoxypropylene (POP) or a copolymer of POE zand POP. The copolymers often terminate in C1 to C12 alkyl groups.

Suitable emulsifiers are widely available under many tradenames including Abil™, Arlacel™, Brij™, Cremophor™, Dehydrol™, Emerest™, Lameform™, Quest PGPH™, Pluronic™, Prosorine™, Span™, Tween™, SF 1228, DC3225C and Q2-5200.

The hydrophilic carrier normally comprises water and can comprise one or more water soluble or water miscible liquids in addition to or replacement for water. The proportion of water in an emulsion according to the present invention is often selected in the range of up to 50%, and particularly from 5 to 40%. Some of the water may be introduced as a solvent for the antiperspirant active.

One class of water soluble or water-miscible solvents comprises short chain monohydric alcohols, e.g. C1 to C4 and especially ethanol or isopropanol, which can impart a deodorising capability to the formulation. A further class of hydrophilic liquids comprises di or polyols, preferably having a melting point of below 40° C., or which are water miscible. Examples of di or polyols include glycol, 1,2 propylene glycol, 1,3 butylene glycol, hexylene glycol, diethylene glycol, dipropylene glycol 2-ethoxyethanol, diethylene glycol monoethylether and triethyleneglycol momethylether. Especially preferred polyols comprise glycerol or sorbitol and related compounds which are capable also of acting as a humectant. The proportion of a mono, di or polyol in the formulation is often selected in the range of up to 15%, and in a number of instances from 0.5 to 12%. conveniently up to about 5% and preferably from about 0.2 to 3%.

Optional ingredients in the invention compositions can include disinfectants, for example at a concentration of up to about 10% w/w. Suitable deodorant actives can comprise deodorant effective concentrations of antiperspirant metal salts, deoperfumes, and/or microbicides, including particularly bactericides, such as chlorinated aromatics, including biguanide derivatives, of which materials known as Igasan DP300™ (triclosan), Triclorban™ and Chlorhexidine warrant specific mention.

A yet other class comprises biguanide salts such as available under the trademark Cosmosil™.

Other optional ingredients include wash-off agents, often present in an amount of up to 10% w/w to assist in the removal of the formulation from skin or clothing. Such wash-off agents are typically non-ionic surfactants such as esters or ethers containing a C8 to C22 alkyl moiety and a hydrophilic moiety which can comprise a polyoxyalkylene group (POE or POP) and/or a polyol.

A further optional constituent of the formulation comprises one or more secondary structurants which can be employed in addition to the primary structurant system, i.e. the sterol plus sterol ester. The amount of such secondary structurants in the formulation is often 0, and usually not more than 15% of the formulation. It is normally not greater than the amount of the primary structurant.

The secondary structurants employable herein can be non-polymeric or polymeric. Non-polymeric structurants, sometimes referred to as gellants, can be selected from fatty acids or salts thereof, such as stearic acid or sodium stearate or 12-hydroxystearic acid. Other suitable gellants can comprise dibenzylidene alditols, e.g. dibenzylidene sorbitol. Further suitable gellants can comprise lanosterol, selected n-acyl amino acid derivatives, including ester and amide derivatives, such as N-lauroyl glutamate dibutylamide, which gellants can be contemplated in conjunction with hydroxystearic acid or an ester or amide derivative thereof. Still further gellants include amide derivatives of di or tribasic carboxylic acids, such as alkyl N,N' dialkylsuccinamides, e.g. dodecyl N,N'-dibutylsuccinamide. Stearyl alcohol and/or a natural plant or animal derived wax or similar synthetic waxes can be employed, if desired, as secondary structurant but are currently not preferred.

Polymeric structurants which can be employed can comprise organo polysiloxane elastomers such as reaction products of a vinyl terminated polysiloxane and a cross linking agent or alkyl or alkyl polyoxyalkylene-terminated poly (methyl substituted) or poly(phenyl substituted) siloxanes. A number of polyamides have also been disclosed as structurants for hydrophobic liquids. Polymers containing both siloxane and hydrogen bonding groups have been disclosed in WO 97/36572 and WO 99/06473. If the composition comprises an aqueous phase, this phase can be structured or thickened by polyacrylamides, polyacrylates or polyalkylene oxides.

The compositions herein can incorporate one or more cosmetic adjuncts conventionally contemplatable for antiperspirant solids or soft solids. Such cosmetic adjuncts can include skin feel improvers, such as talc or finely divided polyethylene, for example in an amount of up to about 10% w/w; skin benefit agents such as allantoin or lipids, for example in an amount of up to 5% w/w; colours; skin cooling agents other than the already mentioned alcohols, such as menthol and menthol derivatives, often in an amount of up to 2% w/w. A commonly employed adjunct comprises a perfume, which is normally present at a concentration of from 0 to 4% and in many formulations from 0.25 to 2%.

The compositions described herein can be produced by conventional processes for making suspension or emulsion solids or soft-solids.

Thus, according to a second aspect of the present invention there is provided process for the production of an antiperspirant stick comprising the steps of:

1. incorporating into a liquid carrier a structurant comprising an effective concentration of a combination of at least one sterol and at least one sterol ester in an amount sufficient to thicken or structure the carrier to produce a solid or soft solid,
2. rendering the structurant-containing mixture or one or more of its constituents mobile at an elevated temperature
3. mixing the liquid carrier with an antiperspirant active to form an antiperspirant-containing mixture, steps 2 and 3 being conducted either before, after or simultaneously with step 1
4. introducing the mobile mixture into a mould which preferably is a dispensing container and
5. cooling or permitting the mobile mixture to cool to a temperature at which it is thickened or structured.

A convenient process sequence for suspension formulations comprises first forming a solution of the sterol and sterol ester in the carrier or mixture of carriers. This is normally carried out by agitating the mixture at an elevated temperature, such as selected within the range of from 50 to 120° C. Both the sterol ester and the sterol can be introduced simultaneously or sequentially into the carrier, at an appropriate temperature and agitation, for example the sterol ester followed by the sterol, or the sterol ester and sterol can be dissolved in aliquots of the carrier which are subsequently blended. Thereafter, particulate antiperspirant active can be blended with the carrier solution and the blend introduced, at a temperature that is often 5 to 10° C. above its setting temperature into its dispensing container, such as a barrel using suitable filling processes and is cooled or allowed to cool to ambient.

In a suitable process for making emulsion formulations, a solution of sterol ester and sterol is formed in the hydrophobic carrier in the manner as for preparation of a suspension stick, and separately an aqueous or hydrophilic phase is prepared, by introduction of antiperspirant active into the phase (if necessary, since such actives can conveniently be supplied in aqueous solution) preferably being heated to a temperature similar to that of the oil phase and thereafter mixed, or alternatively introduced into the oil phase at a rate which maintains the elevated temperature of the mixture and is thereafter filled in a similar manner to that for suspension sticks.

The compositions herein are suitable for applying topically to human skin, and particularly to axillae, thereby reducing observable perspiration.

Thus, according to a third aspect of the present invention, there is provided a method for preventing or reducing perspiration on human skin comprising topically applying to the skin an antiperspirant composition comprising an antiperspirant active, a liquid carrier and a structurant which comprises an effective concentration of a combination of at least one sterol except lanosterol and at least one sterol ester.

Having described the invention in general terms, specific embodiments thereof will be described more fully by way of example only.

In the Examples or Comparisons, the various constituents were as follows:

1) vol sil=cyclomethicone blend DC345 (Dow Corning Inc)
2) PPG-14 Butylether Fluid AP (Amercol).
3) CAB=$C_{12}$–$C_{15}$ alkyl benzoate Finsolv TN (Fintex).
4) ISA=isostearyl alcohol Prisorine 3515 (Unichema).
5a) β Sitosterol (D.R.T)
5b) ultrasitosterol (Kaukas)
5c) β Sitosterol (Acros)
6) γ Oryzanol (Jan Dekker (UK) Ltd)
7) Al/Zr Tetrachlorohydrex glycine complex AZAG 7167 (Summit)
8) Cholesterol (Acros)
9) Dihydro-cholesterol (Sigma)
10) Polydecene Silkflo 364NF (Albemarle)
11) Isopropyl Myristate Estol 1514 (Unichema)
12) Cetyl Dimethicone Copolyol Abil EM90 (Th. Goldschmidt) [emulsifier]
13) 50% aqueous solution of Al/Zr pentachlorohydrate Zirconal 50 (Giulini)
14) Glycerol (Aldrich)
15) Low refractive index AACH (Unilever)
16) Superfino talc (Cyprus Minerals) 57.5% Rezal 36 GPSUF aqueous solution
17) Aluminium zirconium tetrachlorohydrex glycine (fine particle size) Rezal 36 GPSUF aqueous solution
18) Aluminium-Zirconium Glycine complex Summit AZG-375
19) Propylene Glycol (Fisons)
20) Polyglycerol-3 diisostearate Lamemform TGI
21) Polyglycerol-2 dipolyhydroxystearate Dehymuls PGPH
22) Polyglycerol-polyrincinolate Quest PGPR
23) Polyglycerol-2 isostearatePrisorine 3791
24) Polyglycerol-2 diisostearate Prisorine 3792
25) Cyclomethicone blend DC245 (Dow Corning Inc)

Comparisons C1–C10 and Examples 11 to 19

In these Comparisons and Examples, the capability of individual sterols or sterol esters and mixtures of sterol and sterol ester to gel representative hydrophobic solvents is demonstrated. The sterol and/or sterol ester was/were dissolved in the solvent in a glass bottle by heating and stirring. The resulting clear solution was allowed to cool to laboratory temperature without stirring. The product was assessed the following day.

The results are summarised in Table 1 below.

TABLE 1

| Comp or Example | Sterol Sterol Ester | Solvent or mixture | Product * |
|---|---|---|---|
| C1 | 10% cholesterol | Polydecene ([10]) | crystal slush |
| C2 | 10% dihydro-cholesterol | Polydecene ([10]) | crystal slush |
| C3 | 10% β sitosterol | Polydecene ([10]) | soft paste |
| C4 | 10% oryzanol | Polydecene ([10]) | crystals + clear liquid |
| Ex 11 | 5% cholesterol/5% oryzanol | Polydecene ([10]) | hard gel |
| Ex 12 | 5% dihydrocholesterol/5% oryzanol | Polydecene ([10]) | hard gel |
| Ex 13 | 5% β sitosterol/ 5% oryzanol | Polydecene ([10]) | hard gel |
| C5 | 10% cholesterol | 70% volsil ([1]) 30% ISA ([2]) | crystal slush |
| C6 | 10% dihydro-cholesterol | 70% volsil ([1]) 30% ISA ([2]) | crystals + clear liquid |
| C7 | 10% β sitosterol | 70% volsil ([1]) 30% ISA([2]) | crystals + clear liquid |
| C8 | 10% oryzanol | 70% volsil ([1]) 30% ISA ([2]) | crystals + cloudy liquid |
| Ex 14 | 5% cholesterol/5% oryzanol | 70% volsil ([1]) 30% ISA ([2]) | hard gel |
| Ex 15 | 5% dihydrocholesterol/5% oryzanol | 70% volsil ([1]) 30% ISA ([2]) | hard gel |
| Ex 16 | 5% β sitosterol/ 5% oryzanol | 70% volsil ([1]) 30% ISA 9"0 | hard gel |
| C9 | 10% β sitosterol | 60% volsil ([1]) 40% CAB ([4]) | crystal slush |
| C10 | 10% oryzanol | 60% volsil ([1]) 40% CAB ([4]) | crystals + clear liquid |
| Ex 17 | 5% β sitosterol/ 5% oryzanol | 60% volsil ([1]) 40% CAB ([4]) | hard gel |
| Ex 18 | 8% β sitosterol/ 2% oryzanol | 60% volsil ([1]) 40% CAB ([4]) | hard gel |
| Ex 19 | 2% β sitosterol/ 8% oryzanol | 60% volsil ([1]) 40% CAB ([4]) | hard gel |

From Table 1, it can be seen clearly by comparing the comparisons marked with a C and the Examples marked with Ex that the combination of sterol and sterol ester was capable of producing gelation superior to that from either the sterol or the sterol ester alone at the same overall concentration.

Examples 20 to 38

In these Examples, suspension sticks according to the formulations summarised in Table 2 below were made as follows:

The carriers were first combined. The oryzanol (the sterol ester) was introduced into the carriers and dissolved by heating and stirring. Once the oryzanol had dissolved completely, the sterol was introduced and the mixture heated and stirred until a clear solution was obtained. The solution was then allowed to cool under gentle stirring until it had reached a temperature of about 5–10 degrees above its gelling point. The specified particulate antiperspirant active was then stirred in and fully dispersed. The mixture was then poured into stick barrels and allowed to cool and solidify. A number of the sticks were analysed by the methods described hereinbelow and the results summarised in Table 2 below. The evaluations were made after the stick had been stored for at least 24 hours at laboratory room temperature.

assessment showed that all gave lower white deposits on skin than a conventional opaque white solid stick.

From Table 2, it can be observed that suspension sticks having acceptable hardness and only low or very low deposits can be obtained using a combination of a sterol and a sterol ester according to the present invention.

Examples 39 to 55

In these Examples, emulsion sticks according to the formulations summarised in Table 3 below were made as follows:

In the first step, the hydrophobic phase was prepared by combining the cosmetic oils and solvents, the emulsifier introduced and dissolved in a Silverson mixer. The oryzanol

TABLE 2

| Example No Constituent | 20 | 21 | 22 | 23 | 24 | 25 | 26 | 27 | 28 |
|---|---|---|---|---|---|---|---|---|---|
| | Weight % in formulation | | | | | | | | |
| cyclomethicones[1] | 56.0 | 56.0 | 56.0 | 56.0 | 56.0 | 52.0 | 53.0 | 53.0 | 55.5 |
| PPG-14 Butylether[2] | 0.7 | 2.8 | — | 3.5 | — | — | — | — | — |
| $C_{12-15}$ Alkyl Benzoate[3] | 8.4 | 8.4 | 10.5 | 10.5 | 15.0 | 15.0 | 15.0 | — | 12.5 |
| Isostearyl Alcohol[4] | 4.9 | 2.8 | 3.5 | — | — | — | — | 15.0 | — |
| β Sitosterol[5a] | 3.0 | 3.0 | 3.0 | 3.0 | 3.5 | 4.5 | 4.0 | 4.0 | 4.0 |
| Oryzanol[6] | 3.0 | 3.0 | 3.0 | 3.0 | 3.5 | 4.5 | 4.0 | 4.0 | 4.0 |
| AZAG 7167[7] | 24 | 24 | 24 | 24 | 24 | 24 | 24 | 24 | 24 |
| Penetrometer Hardness (mm) | 10.5 | 10.3 | 10.5 | 10.5 | 9.2 | 7.7 | 9.3 | 8.2 | 10.7 |
| Deposits Score Abrasive Paper | n/d | 43 | n/d | 36 | 24 | 25 | 24 | n/d | n/d |
| Deposit Score Black Wool | n/d | 60 | n/d | 52 | 15 | 14 | 17 | n/d | n/d |
| EXAMPLE Constituent | 29 | 30 | 31 | 32 | 33 | 34 | 35 | 36 | 37 |
| | Weight % in formulation | | | | | | | | |
| Cyclomethicone[1] | 53.0 | 50.0 | 50.0 | 50.0 | 50.0 | 56.0 | 56.0 | 55.0 | 55.0 |
| PPG-14 Butylether[2] | — | — | 5.0 | 4.0 | 1.0 | 2.8 | 2.8 | 2.8 | 2.8 |
| $C_{12-15}$ Alkyl Benzoate[3] | 7.5 | 15.0 | 15.0 | 12.0 | 12.0 | 8.4 | 8.4 | 8.4 | 8.4 |
| Isostearyl Alcohol[4] | 7.5 | 5.0 | — | 4.0 | 7.0 | 2.8 | 2.8 | 2.8 | 2.8 |
| β Sitosterol[5a] | 4.0 | 3.0 | 3.0 | 3.0 | 3.0 | 2.1 | 3.9 | — | — |
| Cholesterol[8] | — | — | — | — | — | — | — | 3.5 | — |
| Dihydro-cholesterol[9] | — | — | — | — | — | — | — | — | 3.5 |
| Oryzanol[6] | 4.0 | 3.0 | 3.0 | 3.0 | 3.0 | 3.9 | 2.1 | 3.5 | 3.5 |
| AZAG 7167[7] | 24 | 24 | 24 | 24 | 24.0 | 24.0 | 24.0 | 24.0 | 24.0 |
| Penetrometer Hardness (mm) | 8.4 | 11.8 | 11.7 | 11.6 | 11.1 | 11.0 | 18.2 | 10.4 | 10.6 |
| Deposits Score Abrasive Paper | n/d | 28 | n/d | 26 | n/d | 24 | n/d | 36 | 24 |
| Deposit Score Black Wool | n/d | 11 | n/d | 29 | n/d | 26 | n/d | 63 | 15 |

| EXAMPLE Constituent | 38 | CWS |
|---|---|---|
| | Weight % in formulation | |
| $C_{12-15}$ Benzoate[3] | 62.0 | |
| β Sitosterol[5a] | 7.0 | |
| Oryzanol[6] | 7.0 | |
| AACH water modified[15] | 24.0 | |
| Penetrometer Hardness (mm) | 15.1 | 9.4 |
| Deposits Score Abrasive Paper | 22 | 118 |
| Deposit Score Black Wool | 12 | 186 |

CWS is a conventionally stearyl alcohol and wax-structured white suspension stick Examples 20 to 34, 36 and 37 were hard opaque white sticks. Example 35 was a slightly softer white stick. Example 38 was a hard slightly translucent stick. Qualitative (the sterol ester) was introduced and dissolved by heating and stirring at 5000 rpm. Once the oryzanol had dissolved completely, the sterol was added and the mixture again heated and stirred until a clear solution had been obtained. The solution was then allowed to cool under gentle stirring until it reached a temperature of about 5–10 degrees above its gelling point.

In the second step, the aqueous phase was prepared by combining the antiperspirant solution with the other aqueous phase components. This was heated to the same temperature as the continuous phase solution.

In the third step, the aqueous phase was introduced slowly into the hydrophobic phase was introduced in the Silverson mixer, and maintained at a constantly temperature and at constant shear conditions (8000 rpm). The mixture was sheared for up to 10 minutes, until the aqueous phase had been evenly dispersed. The resulting emulsion was then left to stand and to de-aerate. It was then poured into stick barrels and allowed to cool to laboratory ambient temperature and solidify. A number of the resultant sticks were evaluated for penetration and hardness by the methods described below after the stick had been maintained for at least 24 hours at room temperature. The results are summarised in Table 3 below.

TABLE 3

| Example Constituent | 39 | 40 | 41 | 42 | 43 | 44 | 45 |
|---|---|---|---|---|---|---|---|
|  | Weight % in formulation |  |  |  |  |  |  |
| Continuous phase |  |  |  |  |  |  |  |
| Cyclomethicone($^1$) | 23.5 | 32.4 | 40.0 | 40.0 | 40.0 | 40.0 | 35.0 |
| PPG-14 Butylether($^2$) | — | 5.0 | — | — | — | — | — |
| $C_{12-15}$ Alkyl Benzoate($^3$) | 12.5 | 12.7 | 10.0 | — | — | — | — |
| Isostearyl Alcohol($^4$) | — | — | — | 10.0 | 10.0 | — | — |
| Polydecene($^{10}$) | 11.3 | — | — | — | — | — | — |
| Isopropyl Myristate($^{11}$) | — | — | — | — | — | 10.0 | 15.0 |
| β Sitosterol($^{5a}$) | — | — | — | — | — | — | — |
| β Sitosterol($^{5b}$) | 2.4 | 2.5 | — | 2.5 | — | 2.5 | 2.5 |
| β Sitosterol($^{5c}$) | — | — | 2.5 | — | — | — | — |
| Dihydrocholesterol($^9$) | — | — | — | — | 2.5 | — | — |
| Oryzanol($^6$) | 2.4 | 2.5 | 2.5 | 2.5 | 2.5 | 2.5 | 2.5 |
| Cetyl Dimethicone Copolyol($^{12}$) | 0.9 | 1.0 | 1.0 | 1.0 | 1.0 | 1.0 | 1.0 |
| Aqueous phase |  |  |  |  |  |  |  |
| Zirkonal 50($^{13}$) | 37.6 | 39.9 | 40.0 | 40.0 | 40.0 | 40.0 | 40.0 |
| Glycerol($^{14}$) | 9.4 | 4.0 | 4.0 | — | — | 4.0 | 4.0 |
| water | — | — | — | 4.0 | 4.0 | — | — |
| Penetrometer Hardness (mm) | 16.9 | 17.8 | 17.1 | 22.4 | 26.7 | n/d | 18.8 |
| Deposits Score Abrasive Paper | 22 | 28 | 26 | n/d | 22 | n/d | n/d |
| Deposit Score Black Wool |  | 11 | 14 | n/d | 29 | n/d | n/d |

| Example Constituent | 46 | 47 | 48 | 49 | 50 | 51 | 52 |
|---|---|---|---|---|---|---|---|
|  | Weight % in formulation |  |  |  |  |  |  |
| Continuous phase |  |  |  |  |  |  |  |
| Cyclomethicone($^1$) | 35.0 | 35.0 | 35.0 | 35.0 | 25.0 | 34.0 | 33.0 |
| PPG-14 Butylether($^2$) | — | — | — | — | — | — | — |
| $C_{12-15}$ Alkyl Benzoate($^3$) | 7.5 | — | 15.0 | 7.5 | 25.0 | 7.5 | 7.5 |
| Isostearyl Alcohol($^4$) | — | — | — | — | — | 7.5 | 7.5 |
| Polydecene($^{10}$) | — | — | — | — | — | — | — |
| Isopropyl Myristate($^{11}$) | 7.5 | 15.0 | — | 7.5 | — | — | — |
| β Sitosterol($^{5a}$) | — | — | — | — | — | — | — |
| β Sitosterol($^{5b}$) | — | — | — | — | — | — | — |
| β Sitosterol($^{5c}$) | 2.5 | 2.5 | 2.5 | 2.5 | 2.5 | 3.0 | 3.5 |
| Dihydrocholesterol($^9$) | — | — | — | — | — | — | — |
| Oryzanol($^6$) | 2.5 | 2.5 | 2.5 | 2.5 | 2.5 | 3.0 | 3.5 |
| Cetyl Dimethicone Copolyol($^{12}$) | 1.0 | 1.0 | 1.0 | 1.0 | 1.0 | 1.0 | 1.0 |
| Aqueous Phase |  |  |  |  |  |  |  |

TABLE 3-continued

| Zirkonal 50($^{13}$) | 40.0 | 40.0 | 40.0 | 40.0 | 40.0 | 40.0 | 40.0 |
|---|---|---|---|---|---|---|---|
| Glycerol($^{14}$) | 4.0 | — | — | — | — | — | — |
| water | — | 4.0 | 4.0 | 4.0 | 4.0 | 4.0 | 4.0 |
| Penetrometer Hardness (mm) | 17.0 | 20.7 | 27.4 | 18.2 | 18.5 | 15.6 | 12.5 |
| Deposits Score Abrasive Paper | N/d | 29 | 30 | 31 | n/d | 26 | 25 |
| Deposit Score Black Wool | N/d | 12 | 12 | 8 | n/d | 12 | 12 |

Examples 39 to 52 were all translucent/opaque or opaque medium hard to hard white sticks. Qualitative assessment showed that all gave lower white deposits on skin than a conventional wax-structured white solid stick.

From Table 3, it can be observed that emulsion sticks having acceptable hardness and only low or very low deposits can be obtained using a combination of a sterol and a sterol ester according to the present invention.

Examples 53 to 56

In these Examples, soft solid or semi-solid sticks according to the present invention and having formulations summarised in Table 4 below were made by the following process:

First, the sterol ester (oryzanol), and carrier fluid, wase introduced into a vessel, and heated to 110° C., whilst being sheared by a Silverson mixer at approximately 3000 rpm until the sterol ester had dissolved. Then, the B-Sitosterol was introduced into the vessel, and sheared further until it had dissolved to a clear solution. The mixture was then allowed to cool to about 80° C. and the powders (talc and AZAG) were introduced slowly with high shear mixing in the mixer, at about 6500 rpm until homogeneously mixed. The resultant mixture was then poured into glass jars at fill temperatures specified in Table 4.

TABLE 4

| Example | 53 | 54 | 55 | 56 |
|---|---|---|---|---|
| Constituent | Weight % in formulation |  |  |  |
| AZAG 7167 ($^7$) | 24.0 | 24.0 | 24.0 | 24.0 |
| Cyclomethicone ($^1$) | 54.0 | 55.0 | 54.5 | 53.0 |
| Oryzanol ($^6$) | 1.0 | 0.5 | 0.75 | 1.5 |
| β-Sitosterol ($^{5a}$) | 1.0 | 0.5 | 0.75 | 1.5 |
| Talc ($^{16}$) | 6.0 | 6.0 | 6.0 | 6.0 |
| $C_{12-15}$ Alkyl Benzoate ($^3$) | 14.0 | 14.0 | 14.0 | 14.0 |
| Hardness | 22.7 | n/d | >30 | 17.1 |

From Table 4, it can be seen that the formulations in Examples 53 and 55 were soft solid formulations suitable for dispensing in conventional soft solid applicators in which the material is extruded through an aperture. Example 57 was soft and leaked solvent. Example 56 was a semi-firm solid, possibly more suited to application via a traditional applicator for a solid.

Examples 57 to 73

Further Soft Solid and Solid Formulations were made by the general methods described in the respective previous Examples for such types of material.

TABLE 5

| Example No | 57 | 58 | 59 | 60 | 61 | 62 |
|---|---|---|---|---|---|---|
| cyclomethicone[1] | 15.15 | 25.25 | 8.6 | 38.0 | 38.0 | 9.0 |
| $C_{12-15}$ alkyl benzoate[3] | 10.10 | 22.73 | 3.44 | 7.5 | 7.5 | 3.6 |
| PPG-14 butyl ether[2] | 25.25 | 2.52 | 30.96 | 7.5 | 7.5 | 32.4 |
| Cetyl dimethicone copolyol[12] | 1.00 | 1.00 | 1.0 | 1.0 | 1.0 | 1.0 |
| Oryzanol[6] | 2.50 | 2.50 | 3.0 | 3.0 | 3.0 | 7.0 |
| β-Sitosterol[5c] | 2.50 | 2.50 | 3.0 | 3.0 | 3.0 | 7.0 |
| 57.5% Rezal 36[17] | 43.5 | 43.5 | | 20.0 | 20.0 | |
| Zirconal 50[13] | | | 50.0 | | | 40.0 |
| Water | | | | 9.0 | 5.0 | |
| Propylene Glycol[19] | | | | 3.6 | 15.0 | |
| Hardness (mm) | >50 | >50 | >50 | 32.4 | 14.4 | 15.1 |

| Example No | 63 | 64 | 65 | 66 | 67 | 68 |
|---|---|---|---|---|---|---|
| cyclomethicone[1] | 24.5 | 24.5 | 38.0 | 24.5 | 24.5 | 23.5 |
| $C_{12-15}$ alkyl benzoate[3] | 22.05 | 8.82 | 7.5 | 22.54 | 10.78 | 10.34 |
| Isopropyl myristate[11] | | | 7.5 | 1.96 | 13.72 | 13.16 |
| PPG-14 butyl ether[2] | 2.45 | 15.68 | | | | |
| Cetyl dimethicone copolyol[12] | 1.0 | 1.0 | 1.0 | 1.0 | 1.0 | 1.0 |
| Oryzanol[6] | 5.0 | 5.0 | 3.0 | 5.0 | 5.0 | 4.0 |
| β-Sitosterol[5c] | 5.0 | 5.0 | 3.0 | 5.0 | 5.0 | 4.0 |
| Zirconal 50[13] | 40.0 | 40.0 | | 40.0 | 40.0 | 40.0 |
| Summit AZG-375[18] | | | 20.0 | | | |
| Water | | | 15.0 | | | 4.0 |
| Propylene Glycol[19] | | | 5.0 | | | |
| Hardness (mm) | 9.3 | 9.3 | 11.2 | 8.28 | 7.92 | 12.06 |

| Example No | 69 | 70 | 71 | 72 | 73 |
|---|---|---|---|---|---|
| cyclomethicone[1] | 34.3 | 34.3 | 34.3 | 31.44 | 13.65 |
| $C_{12-15}$ alkyl benzoate[3] | 8.82 | 8.82 | 8.82 | 6.03 | 12.28 |
| Isopropyl myristate[11] | 5.88 | 5.88 | 5.88 | 6.03 | 19.57 |
| PPG-14 butyl ether[2] | | | | | |
| Cetyl dimethicone copolyol[12] | 1.0 | 1.0 | 1.0 | 1.00 | 1.00 |
| Oryzanol[6] | 3.0 | 3.0 | 3.0 | 2.75 | 5.7 |
| β-Sitosterol[5c] | 3.0 | 3.0 | 3.0 | 2.75 | 3.8 |
| Zirconal 50[13] | | | | 40.0 | 40.0 |
| Summit AZG-375[18] | 22.0 | 22.0 | 22.0 | | |
| Water | 16.5 | 11.0 | 11.0 | 10.0 | 4.0 |
| Propylene Glycol[19] | | 11.0 | | | |
| Glycerol[14] | 5.5 | | 11.0 | | |
| Hardness (mm) | 13.74 | 10.71 | 12.36 | 14.5 | 10.9 |

Examples 74 to 81

In these Examples, formulations according to the present invention were made by the general method employed for Examples 39–55 with other emulsifiers or without an explicit emulsifier.

TABLE 6

| Example No | 74 | 75 | 76 | 77 | 78 | 79 | 80 | 81 |
|---|---|---|---|---|---|---|---|---|
| cyclo-methicone[1] | 33.78 | 33.78 | 33.78 | 33.78 | 33.78 | 33.78 | 33.78 | 34.65 |
| Isopropyl myristate[11] | 5.79 | 5.79 | 5.79 | 5.79 | 5.79 | 5.79 | 5.79 | 5.79 |
| Finsolve TN[3] | 8.69 | 8.69 | 8.69 | 8.69 | 8.69 | 8.69 | 8.69 | 8.69 |
| Abil EM90[12] | 1.75 | | | | | | | |
| Lamemform TGI[20] | | | | 0.875 | 1.75 | | | |
| Dehymuls PGPH[21] | | | | 1.75 | 0.875 | | | |
| Quest PGPR[22] | | 1.75 | | | | | | |
| Prisorine 3791[23] | | | | | | 1.75 | 0.875 | |
| Prisorine 3792[24] | | | | | | | 0.875 | |
| Oryzanol[6] | 3.0 | 3.0 | 3.0 | 3.0 | 3.0 | 3.0 | 3.0 | 3.03 |

TABLE 6-continued

| Example No | 74 | 75 | 76 | 77 | 78 | 79 | 80 | 81 |
|---|---|---|---|---|---|---|---|---|
| β-Sitosterol[5c] | 3.0 | 3.0 | 3.0 | 3.0 | 3.0 | 3.0 | 3.0 | 3.03 |
| Zirconal 50[13] | 40.0 | 40.0 | 40.0 | 40.0 | 40.0 | 40.0 | 40.0 | 40.04 |
| water | 4.0 | 4.0 | 4.0 | 4.0 | 4.0 | 4.0 | 4.0 | 4.04 |
| Hardness (mm) | 12.8 | 13.1 | 12.2 | 11.8 | 12.8 | 16.2 | 12.2 | 11.6 |

Examples 82 to 87

In these Examples, the formulations were obtained by the following general method:

A continuous oil phase was prepared by first introducing oryzanol into a mixture of the oils and the emulsifier. The mixture was heated to and then maintained at approximately 95–100° C., with gentle mixing in a Silverson mixer until the oryzanol had dissolved. The β-sitosterol was then introduced and and allowed to dissolve under the same conditions. A disperse phase (also referred to as the internal phase) was prepared by heating a solution of aluminium zirconium active in water or a mixture of water and polyol to a similar temperature as the continuous oil phase. The disperse phase was then introduced slowly into the oil phase whilst progressively increasing the mixing speed of the Silverson mixer. When the disperse phase had been completely introduced, the formulation was mixed at higher speed for a further 5 minutes, then poured in the stick barrels and allowed to cool naturally to ambient laboratory temperature.

TABLE 7

| Example No | 82 | 83 | 84 | 85 | 86 | 87 |
|---|---|---|---|---|---|---|
| Constituent | | | % by Weight | | | |
| DC245[23] | 25.06 | 24.11 | 21.08 | 20.61 | 17.10 | 13.60 |
| Silkflo 364NF[10] | 31.67 | 30.46 | 26.65 | 26.04 | 21.62 | 17.20 |
| Fluid AP[2] | 6.27 | 6.03 | 5.27 | 5.15 | 4.28 | 3.40 |
| Abil EM90[12] | 1 | 1 | 1 | 1 | 1 | 1 |
| Zirkonal 50[13] | 24 | 24 | 40 | 40 | 40 | 40 |
| Glycerol[14] | 6 | 6 | — | — | 10 | 10 |
| water | — | — | — | — | — | 10 |
| β-Sitosterol[5c] | 3 | 4.2 | 3 | 3.6 | 3 | 2.4 |
| Oryzanol[6] | 3 | 4.2% | 3 | 3.6 | 3 | 2.4 |
| Internal phase | 30 | 30 | 40 | 40 | 50 | 60 |
| Hardness (mm) | 12.9 | 11.2 | 11.8 | 10.7 | 10.4 | 14.1 |

Hardness Measurements by Penetrometer

Equipment
  Lab Plant PNR 10 penetrometer
  Seta wax needle, mass=2.5 g cone angle at the point of the needle specified to be 9°10'∓15' (ASTM D1321; IP376; DIN 51579)
Conditions
  Depth limit=50 mm
  Drop time=5 secs
Operational
  Penetration measurements on a stick were performed in the stick barrel. The stick was wound up to above the barrel surface, and then cut to leave a flat, uniform surface. The needle was carefully lowered to the stick surface, and then a penetration hardness measurement was conducted by allowing the needle in its holder to drop under its combined weight of 50 g for a period of 5 seconds after which the penetration depth is noted. This process was carried out at six different points on the stick surface. Each stick was then wound up a further 1 cm, and a new surface was cut. Six more penetration hardness measurements were made.

The hardness reading quoted is the average value of the 12 measurements.

An appropriate hardness for antiperspirant material intended for use in an open-ended dispensing container is less than 30 mm, particularly in the range of 5 to 20 mm.

Measurement of Deposits

The procedure involves instrumentally applying a sample of an AP stick to a substrate using a pay-off rig under standardised conditions and then measuring the mean level of whiteness of the deposits using image analysis.

I) Application of the Sample to the Substrate

Substrates were:
- a: 12×28 cm strip of abrasive grey 3M™ P800 WetorDry™ carborundum paper
- b: 12×28 cm strip of black Worsted wool fabric which is re-enforced with hypoallergenic surgical tape [3M™ Transpore (1527-2)] to give sufficient rigidity.

The AP sticks were previously unused and with domed top surface unaltered.

The pay-off rig comprised a flat base on to which a flat substrate was attached by a clip at each end. The stick was wiped across the substrate under standard conditions—a spring biased standard downward force onto the substrate and speed of motion.

Each stick was temperature conditioned in the laboratory overnight before the measurement was made. The stick was laterally passed across the substrate eight times. The substrate was carefully removed from the rig and the deposit score, i.e. assessment of whiteness, measured 24 hrs later using image analysis.

II) Image Analysis

The measurement was conducted using a Sony™ XC77 Monochrome video camera with a Cosmicar™ 16 mm focal length lens positioned vertically above a black table which was illuminated from a high angle using fluorescent tubes to remove shadowing. The apparatus was initially calibrated using a reference grey card, after the fluorescence tubes had been turned on long enough for them to give a steady light output. The sample substrate with a deposit thereon from the deposit test was placed on the table and the camera used to capture an image. An area of the image was selected and analysed using a Kontron IBAS image analyser. This notionally divided the image into a large array of pixels and measured the grey level of each pixel on a scale of from 0 (black) through to 255 (white). The average of the grey intensity was calculated. This was an indication of the whiteness of the deposit, higher average numbers indicating a whiter deposit.

What is claimed is:

1. An antiperspirant composition comprising an antiperspirant active, a liquid carrier and a structurant including a sterol to thicken or solidify the composition characterised in that the structurant comprises an effective concentration of a combination of at least one sterol and at least one sterol ester.

2. A composition according to claim 1 characterised in that the structurant comprises sterol and sterol ester in a mole ratio of from 6:1 to 1:4, preferably 3:1 to 1:2.

3. A composition according to claim 1 characterised in that the combined weight of the sterol and sterol ester is from 0.5 to 20%.

4. A composition according to any preceding claim characterised in that the sterol comprises 4 fused rings substituted by an aliphatic, cycloaliphatic or aromatic group.

5. A composition according to claim 4 characterised in that the sterol is substituted by a linear or branched saturated or unsaturated aliphatic hydrocarbon containing up to 20.

6. A composition according to claim 5 characterised in that the sterol is β sitosterol or campesterol or cholesterol, or a hydrogenated derivative thereof.

7. A composition according to claim 6 characterised in that the sterol is β sitosterol.

8. A composition according claim 1 characterised in that the sterol ester is a phenolic acid ester.

9. A composition according to claim 8 characterised in that the ring structure of the sterol ester matches the ring structure of the sterol.

10. A composition according to claim 1 characterised in that the sterol ester is substituted by a linear or branched saturated or unsaturated aliphatic hydrocarbon containing up to 20 and preferably from 4 to 14 carbon atoms.

11. A composition according to claim 10 characterised in that the aliphatic hydrocarbon substituent is a branched unsaturated substituent which contains from 5 to 10 carbons.

12. A composition according to claim 11 characterised in that the sterol ester is γ oryzanol.

13. A composition according to claim 1 characterised in that it contains from 1 to 10% by weight of the combined weight of β sitosterol and oryzanol in a mole ratio of from 3:1 to 1:2.

14. A composition according to claim 1 characterised in that the antiperspirant active comprises an aluminium, zirconium or aluminium/zirconium halohydrate, an activated aluminium, zirconium or aluminium/zirconium halohydrate, or an aluminium, zirconium or aluminium/zirconium complex or an activated aluminium, zirconium or aluminium/zirconium complex.

15. A composition according to claim 14 characterised in that the antiperspirant is selected from chlorohydrates of aluminium, zirconium or mixed zirconium-aluminium, and complexes of such chlorhydrates, any of which chlorhydrate or complex is optionally activated.

16. A composition according to claim 14 characterised in that the antiperspirant active is a mixed zirconium-aluminium chlorohydrate, or an activated aluminium chlorohydrate or a complex of a chlorohydrate of aluminium plus zirconium with glycine, optionally activated.

17. A composition according to claim 1 characterised in that the proportion of antiperspirant active is from 5 to 40% by weight.

18. A composition according to claim 1 characterised in that contains a volatile silicone and optionally a non-volatile silicone and/or a liquid non-silicone hydrophobic organic carrier selected from hydrocarbons, hydrophobic aliphatic esters, aromatic esters, hydrophobic alcohols and hydrophobic ethers.

19. A composition according to claim 1 characterised in that it is anhydrous and contains suspended particulate antiperspirant active.

20. A composition according to claim 1 characterised in that the carrier comprises an aqueous phase containing at least a fraction of the antiperspirant active.

21. A composition according to claim 20 characterised in that the aqueous phase contains a di or polyol.

22. A composition according to claim 20 characterised in that it is in the form of an emulsion.

23. A composition according to claim 22 characterised in that the dispersed phase in the emulsion is from 5 to 80% by weight and the continuous phase from 95 to 20% by weight.

24. A composition according to claim 1 characterised in that it contains from 0.1 to 10% by weight of an emulsifier.

25. A composition according to claim 1 characterised in that it contains a humectant selected from glycerol and sorbitol.

26. A process for the production of an antiperspirant stick comprising the steps of
   1. incorporating into a liquid carrier a structurant at an effective concentration and in an amount sufficient to thicken or structure the carrier to produce a solid or soft solid,
   2. rendering the structurant-containing mixture or one or more of its constituents mobile at an elevated temperature
   3. mixing the liquid carrier with an antiperspirant active to form an antiperspirant-containing mixture, steps 2 and 3 being conducted either before, after or simultaneously with step 1
   4. introducing the mobile mixture into a mould which preferably is a dispensing container and
   5. cooling or permitting the mobile mixture to cool to a temperature at which it is thickened or structured. characterised in that the structurant comprises a combination of at least one sterol and at least one sterol ester.

27. A process according to claim 26 characterised in that the sterol and sterol ester are introduced into simultaneously or sequentially into a hydrophobic fraction of the carrier or separate fractions thereof at elevated temperature and mixed until dissolved, and the resultant solution or solutions is shear mixed with the antiperspirant active and any aqueous constituent.

28. A method for preventing or reducing perspiration on human skin comprising topically applying to the skin an antiperspirant composition comprising an antiperspirant active, a liquid carrier and a structurant which comprises an effective concentration of a combination of at least one sterol and at least one sterol ester.

29. A composition according to claim 3, wherein the combined weight of sterol and sterol ester is from 1 to 15%.

30. A composition according to claim 5, wherein the sterol is substituted by a linear or branched saturated or unsaturated aliphatic hydrocarbon containing from 4 to 14 carbon atoms.

* * * * *